United States Patent [19]

Charpentier et al.

[11] Patent Number: 5,723,499
[45] Date of Patent: Mar. 3, 1998

[54] POLYCYCLIC AROMATIC COMPOUNDS AND PHARMACEUTICAL/COSMETIC COMPOSITIONS COMPRISED THEREOF

[75] Inventors: Bruno Charpentier, Biot; Jean-Michel Bernardon, Le Rouret, both of France

[73] Assignee: C.I.R.D. Galderma, Valbonne, France

[21] Appl. No.: 356,913

[22] Filed: Dec. 15, 1994

[30] Foreign Application Priority Data

Dec. 15, 1993 [FR] France .................. 93 15068

[51] Int. Cl.⁶ .................. A01N 31/14; C07D 211/78
[52] U.S. Cl. .................. 514/717; 514/277; 514/357; 514/427; 514/438; 514/461; 568/632; 568/633; 546/309; 546/312; 546/326; 548/560; 548/561; 548/562; 549/79; 549/80; 549/479
[58] Field of Search .................. 514/717, 277, 514/357, 427, 438, 461; 568/632, 633; 546/309, 312, 326; 548/560, 561, 562; 549/79, 479, 80

[56] References Cited

FOREIGN PATENT DOCUMENTS

| 0210929 | 2/1987 | European Pat. Off. |
| 9206948 | 4/1992 | WIPO |
| 9219583 | 11/1992 | WIPO |

OTHER PUBLICATIONS

Bulletin De La Societe Chimique De France, No. 7–8, 1973, Paris, FR, pp. 2384–2388, H. Eustathopoulos et al, No. 425, p. 2386, col. 2, ex. 1.
Chemical Abstracts, vol. 55, No. 26, Dec. 25, 1961, Columbis, Ohio, abstract No. 27238g, N. G. Sidorova et al, vol. 31, 1961, pp. 2014–2017.
CA 80: 27009 1973.

*Primary Examiner*—Paul J. Killos
*Attorney, Agent, or Firm*—Burns, Doane, Swecker & Mathis, L.L.P.

[57] ABSTRACT

Novel pharmaceutically/cosmetically-active polycyclic aromatic compounds have the structural formula (I):

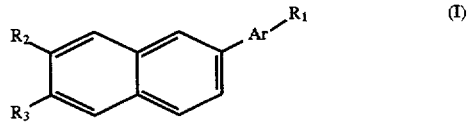

wherein Ar is a radical having one of the formulae (a)–(i):

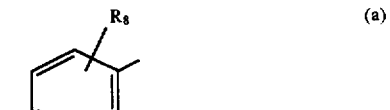
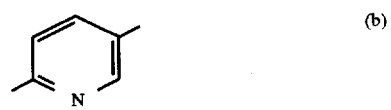
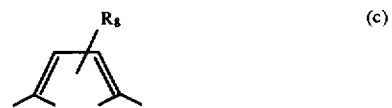
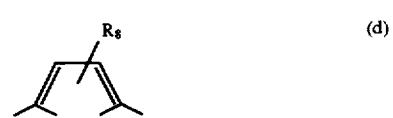
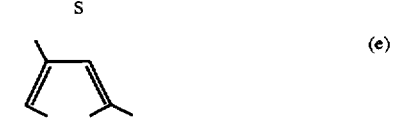
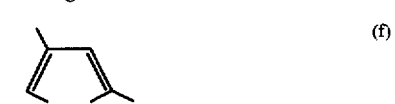
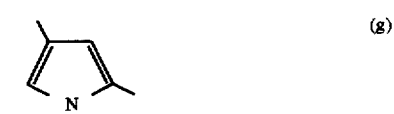
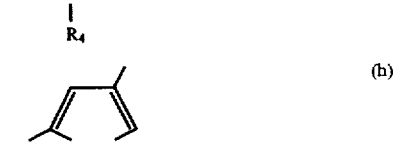
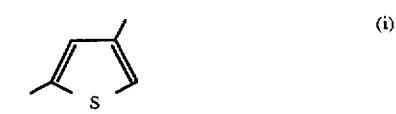

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

57 Claims, 1 Drawing Sheet

POLYCYCLIC AROMATIC COMPOUNDS AND PHARMACEUTICAL/COSMETIC COMPOSITIONS COMPRISED THEREOF

BACKGROUND OF THE INVENTION

1. Field of the Invention

The present invention relates to novel polycyclic aromatic compounds and to pharmaceutical/cosmetic compositions comprised thereof; the subject compounds are especially useful in human or veterinary medicine, or alternatively in cosmetic compositions.

SUMMARY OF THE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degeneration diseases of the connective tissue, for combating skin aging, whether photoinduced or chronologic, and for treating cicatrization disorders. They are also useful for ophthalmological applications, especially for the treatment of corneopathies.

The compounds according to this invention can also be formulated into cosmetic compositions for body and hair care.

Briefly, the polycyclic aromatic compounds according to this invention have the following structural formula (I):

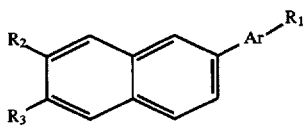

(I)

in which $R_1$ (i) a hydrogen atom, (ii) a radical —$CH_3$, (iii) a radical —$CH_2OH$, (iv) a radical —O—$R_4$, (v) a radical —S(O)$_t$—$R_5$ or (vi) a radical —CO—$R_6$ wherein $R_4$, $R_5$, $R_6$ and t are as defined below; Ar is a radical selected from among those of the following formulae (a)–(i):

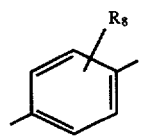

(a)

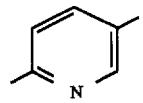

(b)

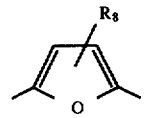

(c)

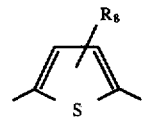

(d)

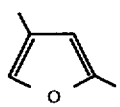

(e)

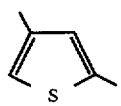

(f)

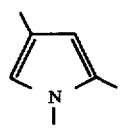

(g)

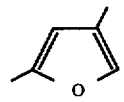

(h)

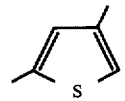

(i)

wherein $R_4$ and $R_8$ are as defined below; $R_2$ is a linear or branched alkyl radical having from 1 to 20 carbon atoms or a cycloaliphatic radical; $R_3$ is (a) a radical —X—$(CH_2)_m$—$R_{10}$, (b) a radical —$(CH_2)_m$—$R_{11}$, (c) a radical —CH=CH—$(CH_2)_n$—$R_{11}$ or (d) a radical —O—$CH_2$—O—$CH_2$—$CH_2$—O—$CH_3$ wherein X, $R_{10}$, $R_{11}$, n and m are as defined below, with the proviso that $R_2$ and $R_3$ may together form, with the adjacent naphthalene nucleus from which they depend, a 5- or 6-membered ring optionally substituted by methyl groups and/or optionally interrupted by an oxygen atom or by a radical —S(O)$_z$— wherein z is as defined below; $R_4$ is a hydrogen atom, a lower alkyl radical or a radical —$(CH_2)_p$—$(CO)_q$—$R_5$ wherein p, q and $R_5$ are as defined below and further wherein the radicals $R_4$ may be identical or different; $R_5$ is a lower alkyl radical or a heterocycle and the radicals $R_5$ may be identical or different; $R_6$ is (a) a hydrogen atom, (b) a lower alkyl radical, (c) a radical of the formula:

$$\diagdown N \diagup \begin{matrix} R' \\ | \\ R'' \end{matrix}$$

wherein R' and R" are as defined below, or (d) a radical —O—$R_7$ wherein $R_7$ is as defined below and further wherein the radicals $R_6$ may be identical or different; $R_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; $R_8$ is a halogen atom, a lower alkyl radical, a hydroxyl radical, a radical —O$R_9$ or —O—CO$R_9$ wherein $R_9$ is as defined below, or a hydrogen atom when $R_2$ is the 1-adamantyl radical and $R_3$ is other than the —OCH$_3$ radical or other than the —OH radical; the radicals $R_9$, which may be identical or different, are each a lower alkyl radical; $R_{10}$ is a hydrogen atom, a lower alkyl radical, an aryl radical, an aralkyl radical, a monohydroxyalkyl radical, a polyhydroxyalkyl radical, a radical —CO—$R_6$ or, but only in the event that m is greater than or equal to 2, a radical of the formula:

wherein R' and R" are as defined below; $R_{11}$ is a hydrogen atom, a monohydroxyalkyl radical, a polyhydroxyalkyl radical, a radical —CO—$R_6$, a radical of the formula:

wherein R' and R" are as defined below, or, but only in the event that m is greater than or equal to 1, a hydroxyl radical, a radical —$OR_9$ or a radical —O—$COR_9$; R' and R", which may be identical or different, are each a hydrogen atom, a lower alkyl radical, a mono- or polyhydroxyalkyl radical, an optionally substituted aryl radical or an amino acid or sugar residue, with the proviso that R' and R" may together form, with the nitrogen atom from which they depend, heterocycle; X is an oxygen or sulfur atom; n is an integer ranging from 0 to 4, inclusive; m is an integer ranging from 0 to 6 inclusive; p is an integer ranging from 1 to 3 inclusive; q is an integer equal to 0 or 1; t is an integer ranging from 0 to 2, inclusive; and z is an integer ranging from 0 to 2, inclusive.

This invention also features the salts of the compounds of formula (I) in the event that the radicals $R_1$ or $R_{10}$ or $R_{11}$ represent a carboxylic acid functional group, or when $R_{10}$ or $R_{11}$ represent an amine functional group, as well as the optical and geometric isomers thereof. When the compounds according to the invention are in the form of salts, they are preferably salts of an alkali or alkaline earth metal or, alternatively, of zinc or of an organic amine.

BRIEF DESCRIPTION OF THE DRAWING

The FIGURE OF DRAWING sets forth reaction schemes/mechanisms illustrating syntheses for the preparation of the polycyclic aromatic compounds according to the present invention.

DETAILED DESCRIPTION OF BEST MODE AND PREFERRED EMBODIMENTS OF THE INVENTION

Figure 1:
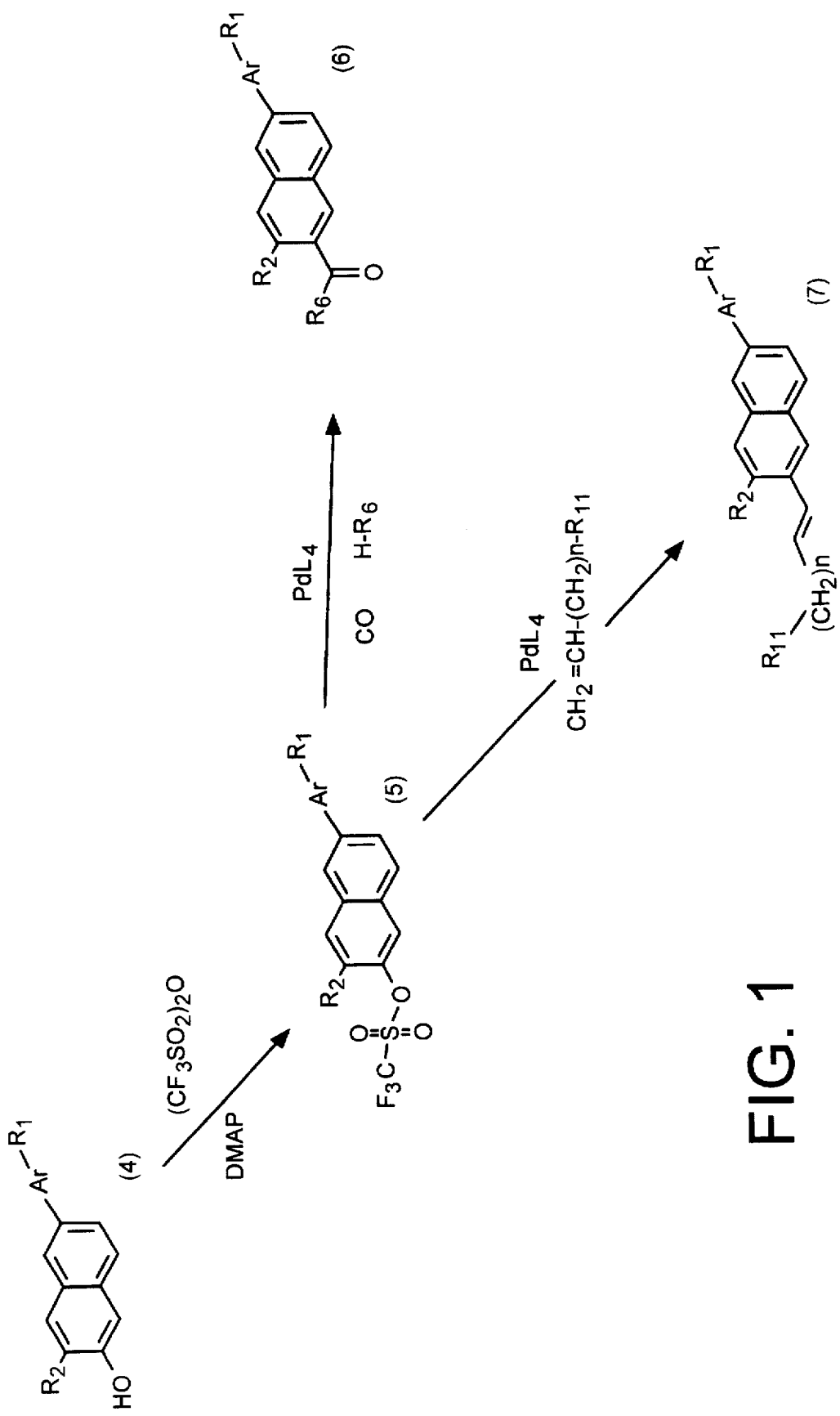

More particularly according to the present invention, by "lower alkyl radical" is intended an alkyl radical having from 1 to 6 carbon atoms, preferably methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "cycloaliphatic radical" is preferably intended a mono- or polycyclic radical, in particular a 1-methylcyclohexyl or 1-adamantyl radical.

By "monohydroxyalkyl radical" is intended a radical preferably having 2 or 3 carbon atoms, especially a 2-hydroxyethyl, 2-hydroxypropyl or 3-hydroxypropyl radical.

By "polyhydroxyalkyl radical" is intended a radical preferably having 3 to 6 carbon atoms and 2 to 5 hydroxyl groups, such as 2,3-dihydroxypropyl, 2,3,4-trihydroxybutyl or 2,3,4,5-tetrahydroxypentyl radicals, or a pentaerythritol residue.

By "aryl radical" is preferably intended a phenyl radical optionally substituted by at least one halogen atom, or a hydroxyl or nitro functional group.

By "aralkyl radical" is preferably intended a benzyl or phenethyl radical optionally substituted by at least one halogen atom, or a hydroxyl or nitro functional group.

By "alkenyl radical" is intended a radical preferably having from 1 to 5 carbon atoms and one or more sites of ethylenic unsaturation, such as, more particularly, the allyl radical.

By "sugar residue" is intended a residue derived especially from glucose, galactose or mannose, or alternatively from glucuronic acid.

By "amino acid residue" is especially intended a residue derived from lysine, glycine or aspartic acid, and by "peptide residue" is more particularly intended a dipeptide or tripeptide residue prepared via the combination of amino acids.

Lastly, by "heterocycle" is preferably intended a piperidino, morpholino, pyrrolidino or piperazino radical, optionally substituted at the 4-position by a $C_1$–$C_6$ alkyl radical or a mono- or polyhydroxyalkyl radical as defined above.

When $R_8$ in formula (I) is a halogen atom, it is preferably a fluorine, chlorine or bromine atom.

Among the compounds of formula (I) according to the present invention, particularly representative are the following:

Ethyl 2-(5,6,7,8-tetrahydro-5,5,8,8-tetramethyl-2-anthryl)-4-thiophenecarboxylate;

2-(5,6,7,8-Tetrahydro-5,5,8,8-tetramethyl-2-anthryl)-4-thiophenecarboxylic acid;

Methyl 4-(5,6,7,8-tetrahydro-5,5,8,8-tetramethyl-2-anthryl)-2-thiophenecarboxylate;

4-(5,6,7,8-Tetrahydro-5,5,8,8,-tetramethyl-2-anthryl)-2-thiophenecarboxylic acid;

Ethyl 6-(5,6,7,8-tetrahydro-5,5,8,8-tetramethyl-2-anthryl)nicotinate;

6-(5,6,7,8-Tetrahydro-5,5,8,8-tetramethyl-2-anthryl) nicotinic acid;

N-Methyl-4-(5,6,7,8-tetrahydro-5,5,8,8-tetramethyl-2-anthryl)-2-pyrrolecarboxylic acid;

4-(5,6,7,8-Tetrahydro-5,5,8,8-tetramethyl-2-anthryl)-2-pyrrolecarboxylic acid;

Methyl 2-hydroxy-4-(5,6,7,8-tetrahydro-5,5,8,8-tetramethyl-2-anthryl)benzoate;

2-Hydroxy-4-(5,6,7,8-tetrahydro-5,5,8,8-tetramethyl-2-anthryl)benzoic acid;

2-Methoxy-4-(5,6,7,8-tetrahydro-5,5,8,8-tetramethyl-2-anthryl)benzoic acid;

2-Hydroxy-4-[7-(1-adamantyl)-6-benzyloxy-2-naphthyl] benzoic acid;

2-Hydroxy-4-[7-(1-adamantyl)-6-hydroxy-2-naphthyl] benzoic acid;

2-Hydroxy-4-[7-(1-adamantyl)-6-hexyloxy-2-naphthyl] benzoic acid;

4-[7-(1-Adamantyl)-6-methoxyethoxymethoxy-2-naphthyl]benzoic acid;

3-Methyl-4-(5,6,7,8-tetrahydro-5,5,8,8-tetramethyl-2-anthryl)benzoic acid;

N-Propyl-4-(5,6,7,8-tetrahydro-5,5,8,8-tetramethyl-2-anthryl)-2-pyrrolecarboxylic acid;

2-Propyloxy-4-(5,6,7,8-tetrahydro-5,5,8,8-tetramethyl-2-anthryl)benzoic acid;

2-Hexyloxy-4-(5,6,7,8-tetrahydro-5,5,8,8-tetramethyl-2-anthryl)benzoic acid;

5-[7-(1-Adamantyl)-6-benzyloxy-2-naphthyl]-2-thiophenecarboxylic acid;

4-[7-(1-Adamantyl)-6-benzyloxy-2-naphthyl]benzoic acid;

2-Chloro-4-(5,6,7,8-tetrahydro-5,5,8,8-tetramethyl-2-anthryl)benzoic acid;

2-Hydroxy-4-[7-(1-adamantyl)-6-(4-fluorobenzyl)oxy-2-naphthyl]benzoic acid;

2-[7-(1-Adamantyl)-6-hydroxy-2-naphthyl]-4-thiophenecarboxylic acid;

2-[7-(1-Adamantyl)-6-methoxy-2-naphthyl]-4-thiophenecarboxylic acid;

Methyl 4-[7-(1-adamantyl)-6-benzyloxycarbonyl-2-naphthyl]benzoate.

According to the present invention, the compounds of formula (I) which are more particularly preferred are those in which Ar represents a radical of formula (a) or (i), $R_6$ represents a radical —$OR_7$ wherein $R_7$ is as defined above, and $R_2$ and $R_3$, together form, with the adjacent naphthalene nucleus from which they depend, a 6-membered ring substituted by methyl groups.

The present invention also features the processes for preparing the compounds of formula (I) via the reaction schemes described below and illustrated in the Figure of Drawing.

The compounds of formula (I) can thus be prepared either:

(i) by a coupling reaction between a halogenated intermediate (1) and a halogenated intermediate (2):

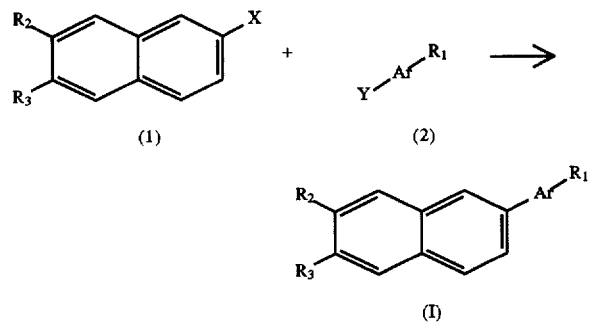

wherein X and Y are each a chlorine, bromine or iodine atom; in a first stage, the halide (1) is converted into a lithium or magnesium compound and then a zinc compound and is coupled to the intermediate (2) in the presence of a nickel or palladium catalyst, according to the biaryl coupling conditions described in E. Negishi et al. *J. Org. Chem.*, 42, 1821 (1977), or (ii) by a coupling reaction between a boronic acid (3) and a halogenated intermediate (2):

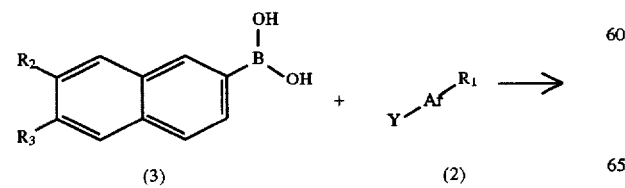

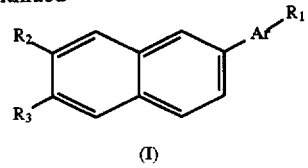

the coupling reaction being carried out in the presence of a palladium catalyst, for example tetrakis-(triphenylphosphine)palladium according to the conditions described in N. Miyaura et al. *Synthetic Communications*, 11 (7), 513–519 (1981); the boronic acid intermediate (3) can itself be prepared, for example from the halogenated intermediate (1) by conversion into a lithium compound, then reaction with trimethyl borate and hydrolysis.

In the aforesaid formulae and reactions $R_1$, $R_3$ and $R_8$ are as defined above in respect of the compounds of formula (I) or are derivatives thereof which are suitably protected such as to be compatible under the coupling conditions. In particular, the substituent $R_3$ is a phenol protected in the form of tert-butyldimethylsilyloxy or an alkoxy radical.

When $R_3$ is a radical —$(CH_2)m$—$CO$—$R_6$ or a radical —$CH=CH$—$(CH_2)n$—$R_{11}$, the compounds are preferably prepared from a phenolic intermediate (4) according to the reaction scheme illustrated in the Figure of Drawing, namely, conversion of the phenolic intermediate (4) into the triflate (5), then nucleophilic substitution in the presence of a palladium catalyst according to the general conditions described in S. Cacchi et al. *Tetrahedron Letters*, 27, 3931–3934 (1986), or in W. J. Scott et al. *J. Org. Chem.*, 50, 2302–2308 (1985).

The present invention also features therapeutic/pharmaceutical applications of the compounds of formula (I).

These compounds exhibit activity in the test for differentiation of mouse embryonic teratocarcinoma cells (F9) (*Cancer Research*, 43, p. 5268 (1983)) and/or in the test for inhibition of ornithine decarboxylase after induction with TPA in mice (*Cancer Research*, 38, p. 793–801 (1978)). These tests demonstrate the activities of the subject compounds for cell differentiation and proliferation applications, respectively.

The compounds according to the invention are particularly suitable in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne;

(2) for treating other types of keratinization disorders, especially ichthyoses, ichthyosiform states, Darier's disease, keratoses palmaris and plantaris, leucoplakias and leucoplakia-like states, skin or mucous (buccal) lichen;

(3) for treating other dermatological conditions associated with a keratinization disorder manifesting an inflammatory and/or immunoallergic component, and, especially, all forms of psoriasis, whether cutaneous, mucous or ungual, and even arthropathic psoriasis, or, alternatively, skin atopy, such as eczema or respiratory atopy or alternatively gingival hypertrophy; the compounds can also be used for treating inflammatory conditions not exhibiting keratinization disorder;

(4) for treating all dermal or epidermal proliferations, whether benign or malignant, whether or not they are of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas;

(5) for treating other dermatological disorders such as bullous dermatoses and collagen diseases;

(6) for treating certain ophthalmological disorders, especially corneopathies;

(7) for repairing or combating skin aging, whether photoinduced or chronologic, or to reduce pigmentations and actinic keratoses, or all pathologies associated with chronologic or actinic aging;

(8) for preventing or curing the stigmas of epidermal and/or dermal atrophy induced by local or systolic corticosteroids, or any other form of skin atrophy;

(9) for preventing or treating cicatrization disorders or for preventing or for repairing vibices;

(10) for combating disorders of the sebaceous function, such as acne hyperseborrhoea or simple seborrhoea;

(11) for the treatment or prevention of cancerous or precancerous states;

(12) for the treatment of inflammatory conditions such as arthritis;

(13) for the treatment of any condition of viral origin at the level of the skin or in general;

(14) for the prevention or treatment of alopecia;

(15) for the treatment of dermatological or general conditions including an immunological component;

(16) for the treatment of conditions of the cardiovascular system, such as arteriosclerosis.

For the aforesaid therapeutic or pharmaceutical applications, the compounds according to the invention can advantageously be used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers. By "D vitamins or derivatives thereof" are intended, for example, the derivatives of vitamin $D_2$ or $D_3$ and in particular 1,25-dihydroxyvitamin $D_3$. By "anti-free radical agents" are intended, for example, α-tocopherol, superoxide dismutase, ubiquinol or certain metal-chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, minoxidil (2,4-diamino-6-piperidinopyrimidine 3-oxide) and derivatives thereof.

The present invention thus also features medicinal compositions containing at least one compound of formula (I), one of its optical or geometric isomers, or one of its pharmaceutically acceptable salts or other derivatives thereof.

The pharmaceutical/therapeutic compositions of this invention, intended especially for the treatment of the aforesaid disease states comprise a carrier which is pharmaceutically acceptable and compatible with the mode or regime of administration selected for the given composition, at least one compound of formula (I), one of its optical or geometric isomers or one of the salts, etc., thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, solutions, elixirs, powders, granules, emulsions, microopheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the regime or rate of 1 to 3 doses per diem.

For topical administration, the pharmaceutical compositions based on compounds according to the invention are more particularly intended for the treatment of the skin and the mucous membranes and can be provided in the form of ointments, creams, milks, pommades, powders, impregnated pads, solutions, gels, sprays, lotions or suspensions. They may also be provided in the form of microopheres or nanospheres or lipid or polymeric vesicles or polymeric patches and hydrogels which permit a controlled release.

These compositions for topical administration may, moreover, be provided either in anhydrous form or in an aqueous form according to the particular clinical indication.

For ocular administration, they are principally collyria.

These compositions for topical or ocular application contain at least one compound of formula (I), or one of its optical or geometric isomers or, alternatively, one of its salts, etc., at a concentration preferably ranging from 0.001% to 5% by weight relative to the total weight of the composition.

The compounds of formula (I) according to the invention also find application in the cosmetic field, in particular for body and hair care and especially for the treatment of skins with acne tendency, for hair regrowth, against loss, for combating the greasy appearance of the skin or the hair, in the protection against the harmful effects of the sun or in the treatment of physiologically dry skins, for preventing and/or for combating photoinduced or chronologic aging.

For cosmetic applications, the compositions of the invention may, moreover, be advantageously used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers, all of these different active agents being as defined above.

The present invention therefore also features cosmetic compositions comprising a carrier which is cosmetically acceptable and suitable for a topical application, at least one compound of formula (I) or one of its optical or geometric isomers or one of its salts. Such cosmetic compositions are advantageously presented in the form of a cream, a milk, a lotion, a gel, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total composition.

The medicinal and cosmetic compositions according to the invention may, in addition, contain inert or even pharmacodynamically or cosmetically active additives or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine-1,1-dioxide) and Phenytoin (5,4-diphenyl-2,4-imidazolidinedione); non-steroidal anti-inflammatory agents; carotenoids and especially β-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as parahydroxybenzoic acid esters, stabilizing agents, moisture regulating agents, pH regulating agents, osmotic pressure modifying agents, emulsifying agents, UV-A and UV-B screening agents, antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of ethyl 2-(5,6,7,8-tetrahydro-5,5,8,8-tetramethyl-2-anthryl)-4-thiophenecarboxylate A solution of 9.5 g (30 mmol) of 5,6,7,8-tetrahydro-5,5,8,8-tetramethyl-2-bromoanthracene was added dropwise to a suspension of 724 mg (30 mmol) of magnesium in 10 ml of THF. Once the addition was completed, the mixture was heated at reflux for one hour. At room temperature 4.1 g (30 mmol) of anhydrous zinc chloride were added and the mixture was stirred for one hour. 5.2 g (22 mmol) of ethyl 2-bromo-4-thiophenecarboxylate and 120 mg (0.22 mmol) of the complex $NiCl_2$/DPPE were then added successively and the mixture was maintained under stirring at room temperature for 12 hours. The reaction medium was poured into ice-cold water, extracted with ethyl ether, the organic phase decanted off, dried over magnesium sulfate and evaporated. The residue obtained was chromatographed on a silica column eluted with a mixture of hexane and dichloromethane (60/40). After evaporation of the solvents, 6.35 g (74%) of the expected ester of melting point 107°–108° C. were recovered.

EXAMPLE 2

Preparation of 2-(5,6,7,8-tetrahydro-5,5,8,8-tetramethyl-2-anthryl)-4-thiophenecarboxylic acid 6.3 g (16 mmol) of the ester prepared in Example 1 and 100 ml of a 2N methanolic sodium hydroxide solution were introduced into a round-bottomed flask and the mixture was heated at reflux for one hour. The reaction medium was evaporated to dryness, the residue taken up in water, acidified to pH 1 with concentrated hydrochloric acid and the solids filtered. The product obtained was recrystallized from an ethyl alcohol/water mixture and 4.5 g (77%) of the expected acid of melting point 223°–225° C. were recovered.

EXAMPLE 3

Preparation of methyl 4-(5,6,7,8-tetrahydro-5,5,8,8-tetramethyl-2-anthryl)-2-thiophene carboxylate Following the basic procedure of Example 1, beginning with 9.5 g (30 mmol) of 5,6,7,8-tetrahydro-5,5,8,8-tetramethyl-2-bromoanthracene and 4.6 g (21 mmol) of methyl 4-bromo-2-thiophenecarboxylate, 2.87 g (36%) of the expected methyl ester were obtained in the form of an amorphous solid.

EXAMPLE 4

Preparation of 4-(5,6,7,8-tetrahydro-5,5,8,8-tetramethyl-2-anthryl)-2-thiophenecarboxylic acid Following the basic procedure of Example 2, beginning with 2.8 g (7.5 mmol) of methyl 4-(5,6,7,8-tetrahydro-5,5,8,8-tetramethyl-2-anthryl)-2-thiophenecarboxylate, 2.4 g (86%) of the expected acid of melting point 207°–208° C. were obtained.

EXAMPLE 5

Preparation of ethyl 6-tetrahydro-5,5,8,8-tetramethyl-2-anthryl)nicotinate

Following the basic procedure of Example 1, beginning with 8.8 g (28 mmol) of 5,6,7,8-tetrahydro-5,5,8,8-tetramethyl-2-bromoanthracene and 3.7 g (20 mmol) of ethyl 6-chloronicotinate, 3.9 g (51%) of the expected ethyl ester of melting point 130°–132° C. were obtained.

EXAMPLE 6

Preparation of 6-(5,6,7,8-tetrahydro-5,5,8,8-tetramethyl-2-anthryl)nicotinic acid Following the procedure of Example 2, beginning with 3.9 g (10 mmol) of the ethyl ester of Example 5, 3.5 g (99%) of the expected acid of melting point 291°–293° C. were obtained.

EXAMPLE 7

Preparation of N-methyl-4-(5,6,7,8-tetrahydro-5,5,8,8-tetramethyl-2-anthryl)-2-pyrrolecarboxylic acid (a) Preparation of 2-trichloroacetylpyrrole 45 g (247 mmol) of trichloroacetyl chloride and 100 ml of ethyl ether were introduced into a three-necked flask. A solution of 15.4 g (230 mmol) of pyrrole in 100 ml of ethyl ether was added dropwise and the mixture was stirred at room temperature for one hour, then a solution of 20 g of potassium carbonate in 60 ml of water was added slowly. The organic phase was decanted off, dried over magnesium sulfate, evaporated, the residue triturated in hexane and filtered. 42.7 g (87%) of the expected compound of melting point 78°–79° C. were recovered.

(b) Preparation of 4-iodo-2-trichloro-acetylpyrrole 8.4 g (39.5 mmol) of 2-trichloroacetylpyrrole and 100 ml of chloroform were introduced into a three-necked flask and under a nitrogen stream and 8.8 g (39.5 mmol) of silver trifluoroacetate and 10.16 g (39.5 mmol) of iodine were added successively. The mixture was stirred at room temperature for one hour, the reaction medium was poured into ice, and extracted with dichloromethane. The organic phase was decanted off, dried over magnesium sulfate and evaporated. The residue obtained was triturated in hexane and filtered; 8.2 g (61%) of the expected compound of melting point 118°–119° C. were recovered.

(c) Preparation of methyl 4-iodo-2-pyrrolecarboxylate 8.2 g (24 mmol) of 4-iodo-2-trichloroacetylpyrrole and 100 ml of methanol were introduced into a round-bottomed flask and 2 g (36 mmol) of sodium methoxide were added. The mixture was stirred at room temperature for four hours, the reaction medium evaporated to dryness, and the residue obtained taken up in water and ethyl ether. The organic phase was decanted off, dried over magnesium sulfate and evaporated. The residue obtained was triturated in heptane and filtered; 4.9 g (81%) of the expected ester of melting point 77°–78° C. were recovered.

(d) Preparation of methyl N-methyl-4-iodo-2-pyrrolecarboxylate 780 mg (25.9 mmol) of sodium hydride (80% in oil) and 20 ml of DMF were introduced into a three-necked flask, a solution of 6.5 g (25.9 mmol) of methyl 4-iodo-2-pyrrolecarboxylate in 50 ml of DMF was added dropwise and the mixture was stirred until gaseous emission ceased. 2.1 ml (33.6 mmol) of iodomethane were then added and the mixture was stirred at room temperature for two hours. The reaction medium was poured into water, extracted with ethyl ether, the organic phase decanted, dried over magnesium sulfate and evaporated. The residue obtained was purified by chromatography on a silica column eluted with a mixture of dichloromethane and hexane (40/60). 4.5 g (65%) of methyl N-methyl-4-iodo-2-pyrrolecarboxylate of melting point 64°–65° C. were recovered.

Preparation of 5,6,7,8-tetrahydro-5,5,8,8-tetramethyl-2-anthrylboronic acid 5 g (15.8 mmol) of 2-bromo-5,6,7,8-tetrahydro-5,5,8,8-tetramethylanthracene and 50 ml of THF were introduced into a three-necked flask and under a nitrogen stream. At −78° C., 7.6 ml (19 mmol) of n-butyllithium (2.5M in hexane) were added dropwise and the mixture was stirred for 15 minutes; at this temperature, 4 ml (35 mmol) of trimethyl borate were added and the mixture stirred for 2 hours. At −50° C., 23 ml of hydrochloric acid (1N) were added and the temperature was permitted to increase to room temperature. The reaction medium was extracted with ethyl ether, the organic phase decanted, dried over magnesium sulfate and evaporated. The residue obtained was triturated in heptane, filtered and dried. 2.8 g (63%) of the expected boronic acid of melting point 220°–225° C. were recovered.

(f) Preparation of methyl N-methyl-4-5,6,7,8-tetrahydro-5,5,8,8-tetramethyl-2-anthryl)-2-pyrrolecarboxylate 231 mg (0.2 mml) of tetrakis-(triphenylphosphine) palladium (0), 50 ml of toluene and 1.75 g (6.6 mmol) of methyl N-methyl-4-iodo-2-pyrrolecarboxylate were introduced into a three-necked flask and under a nitrogen stream and the mixture was stirred at room temperature for 20 minutes. 2.8 g (10 mmol) of 5,6,7,8-tetrahydro-5,5,8,8-tetramethyl-2-anthrylboronic acid and 6.6 ml of an aqueous potassium carbonate solution (2N) were then added and the mixture was heated at reflux for 8 hours. The reaction medium was evaporated to dryness, taken up in water and ethyl ether, the organic phase decanted, dried over magnesium sulfate and evaporated. The residue was purified by chromatography on a silica column eluted with a mixture of dichloromethane and hexane (80/20). 840 mg (47%) of methyl N-methyl-4-(5,6,7,8-tetrahydro-5,5,8,8-tetramethyl-2-anthryl)-2-pyrrolecarboxylate were obtained.

(g) Synthesis of N-methyl-4-5,6,7,8-tetrahydro-5,5,8,8-tetramethyl-2-anthryl)-2-pyrrolecarboxylic acid Following the basic procedure of Example 2, beginning with 840 mg (2.2 mmol) of methyl N-methyl-4-(5,6,7,8-tetrahydro-5,5,8,8-tetramethyl-2-anthryl)-2-pyrrolecarboxylate, 680 mg (84%) of the expected acid of melting point 180°–184° C. were obtained.

EXAMPLE 8

Preparation of 4-(5,6,7,8-tetrahydro-5,5,8,8-tetramethyl-2-anthryl)-2-pyrrolecarboxylic acid (a) Preparation of methyl 4-(5,6,7,8-tetrahydro-5,5,8,8-tetramethyl-2-anthryl)-2-pyrrolecarboxylate Following the basic procedure of Example 7(f), by reacting 2.1 g (7.5 mmol) of 5,6,7,8-tetrahydro-5,5,8,8-tetramethyl-2-anthrylboronic acid with 1.25 g (5 mmol) of methyl 4-iodo-2-pyrrolecarboxylate [prepared in Example 7(c)], 750 mg (42%) of methyl 4-(5,6,7,8-tetrahydro-5,5,8,8-tetramethyl-2-anthryl)-2-pyrrolecarboxylate of melting point 140°–143° C. were obtained.

(b) Synthesis of 4-(5,6,7,8-tetrahydro-5,5,8,8-tetramethyl-2-anthryl)-2-pyrrolecarboxylic acid Following the basic procedure of Example 2, beginning with 750 mg (2 mmol) of methyl 4-(5,6,7,8-tetrahydro-5,5,8,8-tetramethyl-2-anthryl)-2-pyrrolecarboxylate, 180 mg (25%) of the expected acid of melting point 234°–238° C. were obtained.

EXAMPLE 9

Preparation of methyl 2-hydroxy-4-(5,6,7,8-tetrahydro-5,5,8,8-tetramethyl-2-anthryl)benzoate Following the basic procedure of Example 7(f), by reacting 8.5 g (30.3 mmol) of 5,6,7,8-tetrahydro-5,5,8,8-tetramethyl-2-anthrylboronic acid with 5.6 g (20 mmol) of methyl 2-hydroxy-4-iodobenzoate, 5.4 g (69%) of methyl 2-hydroxy-4-(5,6,7,8-tetrahydro-5,5,8,8-tetramethyl-2-anthryl)benzoate of melting point 145°–146° C. were obtained.

EXAMPLE 10

Preparation of 2-hydroxy-4-5,6,7,8-tetrahydro-5,5,8,8-tetramethyl-2-anthryl) benzoic acid Following the basic procedure of Example 2, beginning with 900 mg (2.3 mmol) of methyl 2-hydroxy-4-(5,6,7,8-tetrahydro-5,5,8,8-tetramethyl-2-anthryl)benzoate, 460 mg (53%) of the expected acid of melting point 249°–252° C. were obtained.

EXAMPLE 11

Preparation of 2-methoxy-4-(5,6,7,8-tetramethyl-2-anthryl)benzoic acid (a) Preparation of methyl 2-methoxy-4-(5,6,7,8-tetrahydro-5,5,8,8-tetramethyl-2-anthryl)benzoate 130 mg (4.2 mmol) of sodium hydride (80% in oil) and 20 ml of DMF were introduced into a three-necked flask, a solution of 1.6 g (4.2 mmol) of methyl 2-hydroxy-4-(5,6,7,8-tetrahydro-5,5,8,8-tetramethyl-2-anthryl)benzoate in 50 ml of DMF was added dropwise and the mixture was stirred until gaseous emission ceased. 340 μl (5.5 mmol) of iodomethane were then added and the mixture was stirred at room temperature for two hours. The reaction medium was poured into water, extracted with ethyl ether, the organic phase decanted, dried over magnesium sulfate and evaporated. 1.6 g (96%) of the expected compound was recovered in the form of a colorless oil.

(b) Synthesis of 2-methoxy-4-(5,6,7,8-tetrahydro-5, 5,8,8-tetramethyl-2-anthryl)benzoic acid Following the basic procedure of Example 2, beginning with 1.6 g (4 mmol) of methyl 2-methoxy-4-(5,6,7,8-tetrahydro-5,5,8,8-tetramethyl-2-anthryl)benzoate, 1.2 g (78%) of the expected acid of melting point 177°–178° C. was obtained.

EXAMPLE 12

Preparation of 2-Hydroxy-4-[7-(1-adamantyl)-6-benzyloxy-2-naphthyl]benzoic acid (a) Preparation of 7-(1-adamantyl)-6-benzyloxy-2-bromonaphthalene Following the basic procedure of Example 11, by reacting 12.5 g (35 mmol) of 7-(1-adamantyl)-6-hydroxy-2-bromonaphthalene with 5 ml (42 mmol) of benzyl bromide, 12.5 g (80%) of the expected compound of melting point 150°–151° C. were obtained.

(b) Preparation of 7-(1-adamantyl)-6-benzyloxy-2-naphthylboronic acid

Following the basic procedure of Example 7(e), beginning with 3 g (6.7 mmol) of 7-(1-adamantyl)-6-benzyloxy-2-bromonaphthalene, 2.8 g (100%) of the expected boronic acid were obtained, which acid was employed as is in the synthesis to follow.

(c) Preparation of methyl 2-hydroxy-4-[7-(1-adamantyl)-6-benzyloxy-2-naphthyl]benzoate Following the basic procedure of Example 7(f), by reacting 5.52 g (13.4 mmol) of 7-(1-adamantyl)-6-benzyloxy-2-naphthylboronic acid with 2.46 g (8.8 mmol) of methyl 2-hydroxy-4-iodobenzoate, 1.65 g (36%) of the expected compound was obtained.

(d) Synthesis of 2-hydroxy-4-[7-(1-adamantyl)-6-benzyloxy-2-naphthyl]benzoic acid Following the basic procedure of Example 2, beginning with 930 mg (1.8 mmol) of methyl 2-hydroxy-4-[7-(1-adamantyl)-6-benzyloxy-2-naphthyl]benzoate, 710 mg (79%) of the expected acid of melting point 263°–264° C. were obtained.

EXAMPLE 13

Preparation of 2-hydroxy-4-[7-(1-adamantyl)-6-hydroxy-2-naphthyl]benzoic acid (a) Preparation of methyl 2-hydroxy-4-[7-(1-adamantyl)-6-hydroxy-2-naphthyl]benzoate 1.5 g (2.9 mmol) of methyl 2-hydroxy-4-[7-(1-adamantyl)-6-hydroxy-2-naphthyl]benzoate, 450 g of palladium on carbon (10%) and 50 ml of dioxane were introduced into a reactor. 5 drops of acetic acid were added and the mixture was hydrogenated at 50° C. and at a hydrogen pressure of 6.5 bar for 4 hours. The catalyst was filtered, washed twice with 20 ml of dioxane and the filtrates evaporated. The residue obtained was purified by chromatography on a silica column eluted with a mixture of dichloromethane and hexane (50/50). 830 mg (67%) of the expected compound were recovered.

(b) Synthesis of 2-hydroxy-4-[7-(1-adamantyl)-6-hydroxy-2-naphthyl]benzoic acid

Following the basic procedure of Example 2, beginning with 400 mg (0.9 mmol) of methyl 2-hydroxy-4-[7-(1-adamantyl)-6-hydroxy-2-naphthyl]benzoate, 290 mg (75 of the expected acid of melting point 261°–264° C. were obtained.

EXAMPLE 14

Preparation of 2-hydroxy-4-[7-(1-adamantyl)-6-hexyloxy-2-naphthyl]benzoic acid (a) Preparation of methyl 2-hydroxy-4-[7-(1-adamantyl)-6-hexyloxy-2-naphthyl]benzoate Following the basic procedure of Example 11, by reacting 430 mg (1 mmol) of methyl 2-hydroxy-4-[7-(1-adamantyl)-6-hydroxy-2-naphthyl]benzoate with 180 µl (1.2 mmol) of 6-iodohexane, 280 mg (55%) of methyl 2-hydroxy-4-[7-(1-adamantyl)-6-hexyloxy-2-naphthyl]benzoate were obtained.

(b) Synthesis of 2-hydroxy-4-[7-(1-adamantyl)-6-hexyloxy-2-naphthyl]benzoic acid Following the basic procedure of Example 2, beginning with 100 mg (0.2 mmol) of methyl 2-hydroxy-4-[7-(1-adamantyl)-6-hexyloxy-2-naphthyl]benzoate, 90 mg (92%) of the expected acid of melting point 281°–283° C. were obtained.

EXAMPLE 15

Preparation of 4-[7-(1-adamantyl)-6-methoxyethoxymethoxy-2-naphthyl]benzoic acid (a) Preparation of methyl 4-[7-(1-adamantyl)-6-benzyloxy-2-naphthyl]benzoate Following the basic procedure of Example 7(f), by reacting 2.8 g (6.7 mmol) of 7-(1-adamantyl)-6-benzyloxy-2-naphthyl]boronic acid with 950 mg (4.4 mmol) of methyl 4-bromobenzoate, 1.6 g (72%) of the expected compound was obtained.

(b) Preparation of methyl 4-[7-(1-adamantyl)-6-hydroxy-2-naphthyl]benzoate

Following the basic procedure of Example 13(a), beginning with 1.38 g (2.75 mmol) of methyl 4-[7-(1-adamantyl)-6-benzyloxy-2-naphthyl]benzoate, 980 mg (86%) of methyl 4-[7-(1-adamantyl-6-hydroxy-2-naphthyl]benzoate were obtained in the form of an oil.

Preparation of methyl 4-[7-(1-adamantyl)-6-methoxyethoxymethoxy-2-naphthyl]benzoate Following the basic procedure of Example 12, by reacting 980 mg (2.4 mmol) of methyl 4-[7-(1-adamantyl)-6-hydroxy-2-naphthyl]benzoate with 330 µl (28.6 mmol) of methoxyethoxymethyl chloride, 650 mg (55%) of the expected compound were obtained in the form of an oil.

(d) Synthesis of 4-[7-(1-adamantyl)-6-methoxyethoxymethoxy-2-naphthyl]benzoic acid Following the basic procedure of Example 2, beginning with 650 mg (1.3 mmol) of methyl 4-[7-(1-adamantyl)-6-methoxyethoxymethoxy-2-naphthyl]benzoate, 580 mg (92%) of the expected acid of melting point 234°–236° C. were obtained.

EXAMPLE 16

Preparation of 3-methyl-4-(5,6,7,8-tetrahydro-5,5,8,
8-tetramethyl-2-anthryl)benzoic acid (a) Preparation of 3-methyl-4-iodobenzoic acid 20 g (0.132 mol) of 3-methyl-4-aminobenzoic acid and 175 ml of sulfuric acid (20%) were introduced into a three-necked flask. At −10° C., a solution of 11.9 g (0.172 mol) of sodium nitrite in 50 ml of water was added dropwise and the mixture was stirred for two hours. This solution was introduced dropwise via a dropping funnel cooled to −5° C. into a solution of 35 g (0.211 mol) of potassium iodide, 35.2 g (0.185 mol) of copper iodide and 175 ml of sulfuric acid (20%). The mixture was stirred for eight hours, and the reaction medium filtered. The solids obtained were dissolved in ethyl acetate, washed with water and then with a sodium sulfite solution, dried over magnesium sulfate and evaporated. 24.4 g (70%) of 3-methyl-4-iodobenzoic acid of melting point 205°–210° C. were recovered.

(b) Preparation of methyl 3-methyl-4-iodobenzoate 24.4 g (0.093 mol) of 3-methyl-4-iodobenzoic acid and 250 ml of methanol were introduced into a round-bottomed flask and 2.5 ml of concentrated sulfuric acid were added dropwise. The mixture was heated at reflux for twelve hours, the reaction medium evaporated, taken up in ethyl acetate and water, the organic phase decanted off, dried over magnesium sulfate and evaporated. The residue was triturated in methanol and filtered; 21.9 g (85%) of the expected methyl ester of melting point 58°–59° C. were recovered.

(c) Preparation of methyl 3-methyl-4-(5,6,7,8-tetrahydro-5,5,8,8-tetramethyl-2-anthryl)benzoate Following the basic procedure of Example 7(f), by reacting 2.8 g (10 mmol) of 5,6,7,8-tetrahydro-5,5,8,8-tetramethyl-2-anthrylboronic acid with 1.84 g (6.7 mmol) of methyl 3-methyl-4-iodobenzoate, 1.37 g (53%) of methyl 3-methyl-4-(5,6,7,8-tetrahydro-5,5,8,8-tetramethyl-2-anthryl)benzoate was obtained in the form of a yellow oil.

(d) Synthesis of 3-methyl-4-(5,6,7,8-tetrahydro-5,5,8,8-tetramethyl-2-anthryl)benzoic acid Following the basic procedure of Example 2, beginning with 860 mg (2.2 mmol) of methyl 3-methyl-4-(5,6,7,8-tetrahydro-5,5,8,8-tetramethyl-2-anthryl)benzoate, 770 mg (93%) of the expected acid of melting point 248°–250° C. were obtained.

EXAMPLE 17

Preparation of N-propyl-4-(5,6,7,8-tetrahydro-5,5,8,
8-tetramethyl-2-anthryl)-2-pyrrolecarboxylic acid (a) Preparation of methyl N-propyl-4-iodo-2-pyrrolecarboxylate Following the basic procedure of Example 7(d), by reacting 1.96 g (7.8 mmol) of methyl 4-iodo-2-pyrrolecarboxylate with 940 µl (9.6 mmol) of 3-iodopropane, 1.48 g (64%) of methyl N-propyl-4-iodo-2-pyrrolecarboxylate was obtained in the form of a slightly yellow oil.

(b) Preparation of methyl N-propyl-4-(5,6,7,8-tetrahydro-5,5,8,8-tetramethyl-2-anthryl)-2-pyrrolecarboxylate Following the basic procedure of Example 7(f), by reacting 1.7 g (6 mmol) of 5,6,7,8-tetrahydro-5,5,8,8-tetramethyl-2-anthrylboronic acid with 1.47 g (5 mmol) of methyl N-propyl-4-iodo-2-pyrrolecarboxylate, 450 mg (22%) of methyl N-propyl-4-(5,6,7,8-tetrahydro-5,5,8,8-tetramethyl-2-anthryl)-2-pyrrolecarboxylate were obtained.

(c) Synthesis of N-propyl-4-(5,6,7,8-tetrahydro-5,5,8,8-tetramethyl-2-anthryl)-2-pyrrolecarboxylic acid Following the basic procedure of Example 2, beginning with 450 mg (1.12 mmol) of methyl N-propyl-4-(5,6,7,8-tetrahydro-5,5,8,8-tetramethyl-2-anthryl)-2-pyrrolecarboxylate, 230 mg (54%) of the expected acid of melting point 143°–145° C. were obtained.

EXAMPLE 18

Preparation of 2-propyloxy-4-(5,6,7,8-tetrahydro-5,
5,8,8-tetramethyl-2-anthryl)benzoic acid (a) Preparation of methyl 2-propyloxy-4-(5,6,7,8-tetrahydro-5,5,8,8-tetramethyl-2-anthryl)benzoate Following the basic procedure of Example 12, by reacting 2 g (5.1 mmol) of methyl 2-hydroxy-4-(5,6,7,8-tetrahydro-5,5,8,8-tetramethyl-2-anthryl)benzoate with 600 µl (6.1 mmol) of 3-iodopropane, 1.16 g (54%) of methyl 2-propyloxy- 4-(5,6,7,8-tetrahydro-5,5,8,8-tetramethyl-2-anthryl)benzoate was obtained.

(b) Synthesis of 2-propyloxy-4-(5,6,7,8-tetrahydro-5,5,8,8-tetramethyl-2-anthryl)benzoic acid Following the basic procedure of Example 2, beginning with 1.15 g (2.75 mmol) of methyl 2-propyloxy-4-(5,6,7,8-tetrahydro-5,5,8,8-tetramethyl-2-anthryl)benzoate, 760 mg (68%) of the expected acid of melting point 137°–138° C. were obtained.

EXAMPLE 19

Preparation of 2-hexyloxy-4-(5,6,7,8-tetrahydro-5,5,
8,8-tetramethyl-2-anthryl)benzoic acid (a) Preparation of methyl 2-hexyloxy-4-(5,6,7,8-tetrahydro-5,5,8,8-tetramethyl-2-anthryl)benzoate Following the basic procedure of Example 12, by reacting 2 g (5.1 mmol) of methyl 2-hydroxy-4-(5,6,7,8-tetrahydro-5,5,8,8-tetramethyl-2-anthryl)benzoate with 1.1 ml (6.1 mmol) of 6-iodohexane, 1.67 g (64%) of methyl 2-hexyloxy-4-(5,6,7,8-tetrahydro-5,5,8,8-tetramethyl-2-anthryl)benzoate of melting point 102°–104° C. was obtained.

(b) Synthesis of 2-hexyloxy-4-(5,6,7,8-tetrahydro-5,
5,8,8-tetramethyl-2-anthryl)benzoic acid:

Following the basic procedure of Example 2, beginning with 1.67 g (3.5 mmol) of methyl 2-hexyloxy-4-(5,6,7,8-tetrahydro-5,5,8,8-tetramethyl- 2-anthryl)benzoate, 1.35 g (83%) of the expected acid of melting point 105°–106° C. was obtained.

EXAMPLE 20

Preparation of 5-[7-(1-adamantyl)-6-benzyloxy-2-naphthyl]-2-thiophenecarboxylic acid (a) Preparation of methyl 5-[7-(1-adamantyl)-6-benzyloxy-2-naphthyl]-2-thiophenecarboxylate Following the basic procedure of Example 7(f), by reacting 1.5 g (3.6 mmol) of 7-(1-adamantyl)-6-benzyloxy-2- naphthylboronic acid, with 400 mg (1.8 mmol) of methyl 5-bromo-2-thiophenecarboxylate, 600 mg (65%) of the expected compound of melting point 170°–171° C. were obtained.

(b) Synthesis of 5-[7-(1-adamantyl)-6-benzyloxy-2-naphthyl]-2-thiophenecarboxylic acid Following the basic procedure of Example 2, beginning with 600 mg (1.2 mmol) of methyl 5-[7-(1-adamantyl)-6-benzyloxy-2-naphthyl]-2-thiophenecarboxylate, 460 mg (79%) of the expected acid of melting point 271°–273° C. were obtained.

EXAMPLE 21

Preparation of 4-[7-(1-adamantyl)-6-benzyloxy-2-naphthyl]benzoic acid (a) Preparation of methyl 4-[7-(1-adamantyl)-6-benzyloxy-2-naphthyl]benzoate Following the basic procedure of Example 7(f), by reacting 1.5 g (3.6 mmol) of 7-(1-adamantyl)-6-benzyloxy-2-naphthylboronic acid with 500 mg (1.9 mmol), of methyl 4-iodobenzoate, 320 mg (33%) of the expected compound of melting point 170°–173° C. were obtained.

(b) Synthesis of 4-[7-(1-adamantyl)-6-benzyloxy-2-naphthyl]benzoic acid

Following the basic procedure of Example 2, beginning with 320 mg (0.6 mmol) of methyl 4-[7-(1-adamantyl)-6-benzyloxy-2-naphthyl]benzoate, 195 mg (63%) of the expected acid of melting point 305°–310° C. were obtained.

EXAMPLE 22

Preparation of 2-chloro-4-(5,6,7,8-tetrahydro-5,5,8,8-tetramethyl-2-anthryl) benzoic acid (a) Preparation of 2-chloro-4-iodobenzoic acid Following the basic procedure of Example 16(a), beginning with 10 g (58.3 mmol) of 2-chloro-4-aminobenzoic acid, 14.26 g (86%) of 2-chloro-4-iodobenzoic acid were recovered.

(b) Preparation of methyl 2-chloro-4-iodobenzoate

Following the basic procedure of Example 16(b), beginning with 13.9 g (49.2 mmol) of 2-chloro-4-iodobenzoic acid, 11.52 g (79%) of the expected methyl ester were obtained in the form of an oil.

(c) Preparation of methyl 2-chloro-4-(5,6,7,8-tetrahydro-5,5,8,8-tetramethyl-2-anthryl)benzoate Following the basic procedure of Example 7(f), by reacting 2.8 g (9.9 mmol) of 5,6,7,8-tetrahydro-5,5,8,8-tetramethyl-2-anthrylboronic acid with 2.5 g (8.27 mmol) of methyl 2-chloro-4-iodobenzoate, 1.8 g (67%) of the expected methyl ester was obtained.

(d) Synthesis of 2-chloro-4-(5,6,7,8-tetrahydro-5,5,8,8-tetramethyl-2-anthryl)benzoic acid Following the basic procedure of Example 2, beginning with 2.2 g (5.4 mmol) of methyl 2-chloro-4-(5,6,7,8-tetrahydro-5,5,8,8-tetramethyl-2-anthryl)benzoate, 2.1 g (99%) of the expected acid of melting point 213°–215° C. were obtained.

EXAMPLE 23

Preparation of 2-hydroxy-4-[7-(1-adamantyl)-6-(4-fluorobenzyl)oxy-2-naphthyl]benzoic acid:

(a) Preparation of 7-(1-adamantyl)-6-(4-fluorobenzyl)oxy-2-bromonaphthalene

Following the basic procedure of Example 11, by reacting 1.1 g (3 mmol) of 7-(1-adamantyl)-6-hydroxy-2-bromonaphthalene with 420 μl (3.3 mmol) of 4-fluorobenzyl bromide, 1.2 g (86%) of the expected compound was obtained in the form of a colorless oil.

(b) Preparation of 7-(1-adamantyl)-6-(4-fluorobenzyl)oxy-2-naphthylboronic acid

Following the basic procedure of Example 7(e), beginning with 1.14 g (2.45 mmol) of 7-(1-adamantyl)-6-(4-fluorobenzyl)oxy-2-bromonaphthalene, 560 mg (57%) of the expected boronic acid were obtained.

(c) Preparation of methyl 2-hydroxy-4-[7-(1-adamantyl)-6-(4-fluorobenzyl)oxy-2-naphthyl]benzoate Following the basic procedure of Example 7(f), by reacting 560 mg (1.41 mmol) of 7-(1-adamantyl)-(4-fluorobenzyl) oxy-2-naphthylboronic acid with 330 mg (1.17 mmol) of methyl 2-hydroxy-4-iodobenzoate, 490 mg (78%) of the expected ester of melting point 189°–191° C. were obtained.

(d) Synthesis of 2-hydroxy-4-[7-(1-adamantyl)-6-(4-fluorobenzyl)oxy-2-naphthyl]benzoic acid Following the basic procedure of Example 2, beginning with 490 mg (0.91 mmol) of methyl 2-hydroxy-4-[7-(1-adamantyl)-6-(4-fluorobenzyl)oxy-2-naphthyl]benzoate, 440 mg (92%) of the expected acid of melting point 240°–241° C. were obtained.

EXAMPLE 24

Preparation of 2-[7-(1-adamantyl)-6-(hydroxy-2-naphthyl]-4-thiophenecarboxylic acid Preparation of 7-(1-adamantyl)-6-tert-butyldimethylsilyloxy-2-bromonaphthalene 11.9 g (33.3 mmol) of 7-(1-adamantyl)-6-hydroxy-2-bromonaphthalene, 120 ml of DMF, 5.1 ml (36.6 mmol) of triethylamine and 203 mg of 4-dimethylaminopyridine were introduced successively into a three-necked flask. A solution of 5.52 g (36.6 mmol) of tert-butyldimethylsilyl chloride was added dropwise and the mixture was stirred at room temperature for 12 hours. The reaction medium was poured into water, extracted with ethyl ether, the organic phase decanted, dried over magnesium sulfate and evaporated. The residue obtained was purified by chromatography on a silica column eluted with heptane; 12 g (76%) of 7-(1-adamantyl)-6-tert-butyldimethylsilyloxy-2-bromonaphthalene of melting point 120°–121° C. were recovered.

(b) Preparation of 7-(1-adamantyl)-6-tert-butyldimethylsilyloxy-2-naphthylboronic acid Following the basic procedure of Example 7(e), beginning with 11.9 g (25.4 mmol) of 7-(1-adamantyl)-6-tert-butyldimethylsilyloxy-2-bromonaphthalene, 8.37 g (75%) of the expected boronic acid of melting point 221°–222° C. were obtained.

(c) Preparation of ethyl 2-[7-adamantyl)-6-tert-butyldimethyl-silyloxy-2-naphthyl]-4-thiophenecarboxylate Following the basic procedure of Example 7(f), by reacting 8.37 g (19.2 mmol) of 7-(1-adamantyl)-6-tert-butyldimethylsilyloxy-2-naphthylboronic acid with 4.45 g (18.9 mmol) of ethyl 2-bromo-4-thiophenecarboxylate, 8.87 g (86%) of the expected ethyl ester of melting point 75°–76°C. were obtained.

(d) Synthesis of 2-[7-(1-adamantyl)-6-hydroxy-2-naphthyl]-4-thiophenecarboxylic acid Following the basic procedure of Example 2, beginning with 550 mg (1 mmol) of ethyl 2-[7-(1-adamantyl)-6-tert-butyldimethylsilyloxy-2-naphthyl]-4-thiophenecarboxylate, 186 mg (46%) of the expected acid of melting point 312°–314° C. were obtained.

EXAMPLE 25

Preparation of 2-[7-(1-adamantyl)-6-(methoxy-2-naphthyl]-4-thiophenecarboxylic acid

(a) Preparation of ethyl 2-[7-(1-adamantyl)-6-hydroxy-2-naphthyl]-4-thiophenecarboxylate 8.29 g (15.2 mmol) of ethyl 2-[7-(1-adamantyl)-6-tert-butyldimethylsilyloxy-2-naphthyl]-4-thiophenecarboxylate and 60 ml of THF were introduced into a round-bottomed flask. A solution of 15.2 ml (16.6 mmol) of tetrabutylammonium fluoride in THF (1.1N) was added dropwise and the mixture was stirred at room temperature for 2 hours. The reaction medium was poured into water, extracted with ethyl ether, the organic phase decanted, dried over magnesium sulfate and evaporated. The residue obtained was triturated in heptane, filtered and dried. 6.12 g (93%) of ethyl 2-[7-(1-adamantyl)-6-hydroxy-2-naphthyl]-4-thiophenecarboxylate of melting point 199°–200° C. were recovered.

(b) Preparation of ethyl 2-[7-(1adamantyl)-6-methoxy-2-naphthyl]-4-thiophenecarboxylic Following the basic procedure of Example 11, by reacting 1 g (2.31 mmol) of ethyl 2-[7-(1-adamantyl)-6-hydroxy-2-naphthyl]-4-thiophenecarboxylate with 158 µl (2.54 mmol) of iodomethane, 632 mg (61%) of the expected compound of melting point 159°–160° C. were obtained.

(c) Synthesis of 2-[7-(1-adamantyl)-6-methoxy-2-naphthyl]-4-thiophenecarboxylic acid Following the basic procedure of Example 2, beginning with 625 mg (1.4 mmol) of ethyl 2-[7-(1-adamantyl)-6-methoxy-2-naphthyl]-4-thiophenecarboxylate, 469 mg (80%) of the expected acid of melting point 314°–316°C. were obtained.

EXAMPLE 26

Preparation of ethyl 2-[7-(1-adamantyl)-6-(benzyloxycarbonyl-2-naphthyl]-4-thiophenecarboxylate

(a) Preparation of ethyl 2-[7-(1-adamantyl)-6-trifluoromethyl-sulfonyloxy-2-naphthyl]-4-thiophenecarboxylate 2.4 ml (14.2 mmol) of trifluoro-methanesulfonic anhydride were added dropwise to a solution, cooled to −78° C., of 5.11 g (11.8 mmol) of ethyl 2-[7-(1-adamantyl)-6-hydroxy-2-naphthyl]-4-thiophenecarboxylate, 2.85 ml (35.4 mmol) of pyridine and 14 mg of 4-dimethylaminopyridine in 100 ml of dichloromethane and the mixture was stirred at room temperature for 12 hours. The reaction medium was poured into ice-cold water, extracted with ethyl ether, the organic phase decanted off, washed with a saturated sodium chloride solution, dried over magnesium sulfate and evaporated. The residue obtained was purified by chromatography on a silica column eluted with a mixture of dichloromethane and heptane (40/60). 1.55 g (26%) of ethyl 4-[7-(1-adamantyl)-6-trifluoromethylsulfonyloxy- 2-naphthyl]-4-thiophenecarboxylate of melting point 133°–134° C. were recovered.

(b) Preparation of ethyl 2-[7-(1-adamantyl)-6-benzyloxycarbonyl-2-naphthyl]-4-thiophenecarboxylate:

1.54 g (3 mmol) of ethyl 4-[7-(1-adamantyl)-6-trifluoromethylsulfonyloxy-2-naphthyl]-4-thiophenecarboxylate, 845 µl (6 mmol) of triethylamine, 34 mg (5 mol%) of palladium acetate, 168 mg (0.3 mmol) of diphenylphosphineferrocene, 3.15 ml (30 mmol) of benzyl alcohol and 50 ml of DMF were introduced successively into a reactor. The mixture was heated to 70° C. and subjected to a carbon monoxide pressure of 2.5 bar for 3 hours. The reaction medium was poured into a saturated aqueous sodium chloride solution, extracted with ethyl ether, the organic phase decanted, dried over magnesium sulfate and evaporated. The residue obtained was purified by chromatography on a silica column eluted with a mixture of ethyl acetate and heptane (10/90). 472 mg (28%) of ethyl 2-[7-(1-adamantyl)-6-benzyloxycarbonyl-2-naphthyl]-4-thiophenecarboxylate of melting point 98°–100° C. were recovered.

(c) Synthesis of ethyl 2-[7-(1-adamantyl)-6-benzyloxycarbonyl-2-naphthyl]-4-thiophenecarboxylate Following the basic procedure of Example 2, beginning with 462 mg (0.84 mmol) of ethyl 2-[7-(1-adamantyl)-6-benzyloxycarbonyl-2-naphthyl]-4-thiophenecarboxylate, 419 mg (95%) of the expected acid of melting point 205°–207° C. were obtained.

EXAMPLE 27

Preparation of methyl 4-[7-(1-adamantyl)-6-(benzyloxycarbonyl-2-naphthyl]benzoate

(a) Preparation of methyl 4-[7-(1-adamantyl)-6-trifluoromethylsulfonyloxy-2-naphthyl]benzoate Following the basic procedure of Example 26(a), by reacting 5.5 g (13.3 mmol) of methyl 4-[7-(1-adamantyl)-6-hydroxy-2-naphthyl]benzoate (preparation described in EP-0,210,929) with 2.7 ml (16 mmol) of trifluoromethanesulfonic anhydride, 1.94 g (27%) of methyl 4-[7-(1-adamantyl)-6-trifluoromethylsulfonyloxy-2-naphthyl]benzoate of melting point 226°–227° C. were obtained.

(b) Synthesis of methyl 4-[7-(1-adamantyl)-6-benzyloxycarbonyl-2-naphthyl]benzoate Following the basic procedure of Example 26(b), beginning with 1.91 g (3.5 mmol) of methyl 4-[7-(1-adamantyl) -6-trifluoromethylsulfonyloxy-2-naphthyl]benzoate, 720 mg (40%) of methyl 4-[7-(1-adamantyl)-6-benzyloxycarbonyl-2-naphthyl]benzoate of melting point 143°–144° C. were obtained.

EXAMPLE 28

In this example, various specific formulations based on the compounds according to the invention are illustrated.

(A) ORAL ROUTE:

(a) 0.2 g Tablet:

| | |
|---|---|
| (i) Compound prepared in Example 6 | 0.001 g |
| (ii) Starch | 0.114 g |
| (iii) Dicalcium phosphate | 0.020 g |
| (iv) Silica | 0.020 g |
| (v) Lactose | 0.030 g |
| (vi) Talc | 0.010 g |
| (vii) Magnesium stearate | 0.005 g |

(b) Oral suspension in 5 ml ampoules:

| | |
|---|---|
| (i) Compound prepared in Example 5 | 0.001 g |
| (ii) Glycerin | 0.500 g |
| (iii) Sorbitol at 70% | 0.500 g |
| (iv) Sodium saccharinate | 0.010 g |
| (v) Methyl parahydroxybenzoate | 0.040 g |
| (vi) Flavoring | qs |
| (vii) Purified water | qs 5 ml |

(c) 0.8 g Tablet:

| | |
|---|---|
| (i) Compound of Example 2 | 0.500 g |
| (ii) Pregelatinized starch | 0.100 g |
| (iii) Microcrystalline cellulose | 0.115 g |
| (iv) Lactose | 0.075 g |
| (v) Magnesium stearate | 0.010 g |

(d) Oral suspension in 10 ml ampoules:

| | |
|---|---|
| (i) Compound of Example 4 | 0.200 g |
| (ii) Glycerin | 1.000 g |
| (iii) Sorbitol at 70% | 1.000 g |
| (iv) Sodium saccharinate | 0.010 g |
| (v) Methyl parahydroxybenzoate | 0.080 g |
| (vi) Flavoring | qs |
| (vii) Purified water | qs 10 ml |

(B) TOPICAL ROUTE:

(a) Ointment:

| | |
|---|---|
| (i) Compound of Example 6 | 0.020 g |
| (ii) Isopropyl myristate | 81.700 g |
| (iii) Fluid paraffin oil | 9.100 g |
| (iv) Silica ("Aerosil 200" marketed by DEGUSSA) | 9.180 g |

(b) Ointment:

| | |
|---|---|
| (i) Compound of Example 2 | 0.300 g |
| (ii) Petroleum jelly | 100 g |

(c) Nonionic water-in-oil cream:

| | |
|---|---|
| (i) 6-[7-tert-butyl-6-(2-hydroxypropyl-2-naphthyl]nicotinic acid | 0.100 g |
| (ii) Mixture of emulsive lanolin alcohols, waxes and oils ("anhydrous Eucerin" marketed by BDF) | 39.900 g |
| (iii) Methyl parahydroxybenzoate | 0.075 g |
| (iv) Propyl parahydroxybenzoate | 0.075 g |
| (v) Sterile demineralized water | qs 100 g |

(d) Lotion:

| | |
|---|---|
| (i) 6-(7-tert-butyl-6-methoxycarbonylmethyloxy-2-naphthyl)-nicotinic acid | 0.100 g |
| (ii) Polyethylene glycol (PEG 400) | 69.900 g |
| (iii) Ethanol at 95% | 30.000 g |

(e) Hydrophobic ointment:

| | |
|---|---|
| (i) 6-(7-tert-butyl-6-carboxymethyloxy-2-naphthyl) nicotinic acid | 0.300 g |
| (ii) Isopropyl myristate | 36.400 g |
| (iii) Silicone oil ("Rhodorail 47 V 300" marketed by RHONE-POULENC) | 36.400 g |
| (iv) Beeswax | 13.600 g |
| (v) Silicone oil ("Abil 300.000 cst" marketed by GOLDSCHMIDT) | 100 g |

(f) Nonionic oil-in-water cream:

| | |
|---|---|
| (i) Compound of Example 5 | 1.000 g |
| (ii) Cetyl alcohol | 4.000 g |
| (iii) Glycerol monostearate | 2.500 g |
| (iv) PEG 50 stearate | 2.500 g |
| (v) Shea butter | 9.200 g |
| (vi) Propylene glycol | 2.000 g |
| (vii) Methyl parahydroxybenzoate | 0.075 g |
| (viii) Propyl parahydroxybenzoate | 0.075 g |
| (ix) Sterile demineralized water | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polycyclic aromatic compound having the structural formula (I):

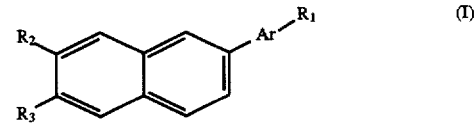

in which $R_1$ (i) a hydrogen atom, (ii) a radical $—CH_3$, (iii) a radical $—CH_2OH$, (iv) a radical $—O—R_4$, (v) a radical $—S(O)_t—R_5$ or (vi) a radical $—CO—R_6$ wherein $R_4$, $R_5$, $R_6$ and t are as defined below; Ar is a radical selected from among those of the following formulae (a)–(i):

-continued

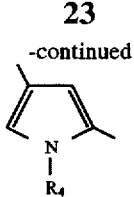 (g)

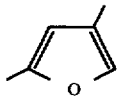 (h)

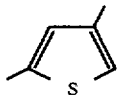 (i)

wherein $R_4$ and $R_8$ are as defined below; $R_2$ is a linear or branched alkyl radical having from 1 to 20 carbon atoms or a cycloaliphatic radical; $R_3$ is (a) a radical —X—$(CH_2)_m$—$R_{10}$, (b) a radical —$(CH_2)_m$—$R_{11}$, (c) a radical —CH=CH—$(CH_2)_n$—$R_{11}$ or (d) a radical —O—$CH_2$—O—$CH_2$—$CH_2$—O—$CH_3$ wherein X, $R_{10}$, $R_{11}$, n and m are as defined below, with the proviso that $R_2$ and $R_3$ may together form, with the adjacent naphthalene nucleus from which they depend, a 5- or 6-membered ring optionally substituted by methyl groups and/or optionally interrupted by an oxygen atom or by a radical —$S(O)_z$— wherein z is as defined below; $R_4$ is a hydrogen atom, a lower alkyl radical or a radical —$(CH_2)_p$—$(CO)_q$—$R_5$ wherein p, q and $R_5$ are as defined below and further wherein the radicals $R_4$ may be identical or different; $R_5$ is a lower alkyl radical or a heterocycle and the radicals $R_5$ may be identical or different; $R_6$ is (a) a hydrogen atom, (b) a lower alkyl radical, (c) a radical of the formula:

wherein R' and R" are as defined below, or (d) a radical —O—$R_7$, wherein $R_7$ is as defined below and further wherein the radicals $R_6$ may be identical or different; $R_7$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue, or an amino acid or peptide residue; $R_8$ is a halogen atom, a lower alkyl radical, a hydroxyl radical, a radical —$OR_9$ or —O—$COR_9$ wherein $R_9$ is as defined below, or is hydrogen only when $R_2$ is 1-adamantyl and $R_3$ can only be selected from the group consisting of (a) a radical —X—$(CH_2)_m$—$R_{10}$ when $R_{10}$ is an aralkyl radical; (b) a radical $(CH_2)_m$—$R_{11}$ where $R_{11}$ is $COR_6$, (c) is a radical —CH=CH—$(CH_2)$—$R_{11}$ and (d) a radical—O—$CH_2$—O—$CH_2$—$CH_2$—O—$CH_3$ wherein x, n and m are defined below; the radicals $R_9$, which may be identical or different, are each a lower alkyl radical; $R_{10}$ is a hydrogen atom, a lower alkyl radical, an aryl radical, an aralkyl radical, a monohydroxyalkyl radical, a polyhydroxyalkyl radical, a radical —CO—$R_6$ or, but only in the event that m is greater than or equal to 2, a radical of the formula:

wherein R' and R" are as defined below; $R_{11}$ is a hydrogen atom, a monohydroxyalkyl radical, a polyhydroxyalkyl radical, a radical —CO—$R_6$, a radical of the formula:

wherein R' and R" are as defined below, or, but only in the event that m is greater than or equal to 1, a hydroxyl radical, a radical —$OR_9$ or a radical —O—$COR_9$; R' and R", which may be identical or different, are each a hydrogen atom, a lower alkyl radical, a mono- or polyhydroxyalkyl radical, an optionally substituted aryl radical or an amino acid or sugar residue, with the proviso that R' and R" may together form, with the nitrogen atom from which they depend, a heterocycle; X is an oxygen or sulfur atom; n is an integer ranging from 0 to 4, inclusive; m is an integer ranging from 0 to 6 inclusive; p is an integer ranging from 1 to 3 inclusive; q is an integer equal to 0 or 1; t is an integer ranging from 0 to 2, inclusive; and z is an integer ranging from 0 to 2, inclusive; or a pharmaceutically/cosmetically acceptable salt or optical or geometric isomer thereof,
wherein if Ar is

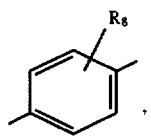 (a)

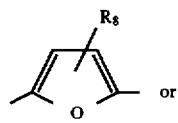 (c)

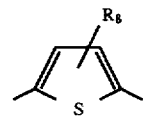 (d)

and $R_1$ is a hydrogen atom, then $R_8$ is not a methyl radical.

2. A polycyclic aromatic compound as defined by claim 1, wherein formula (I), Ar has the structure (a).

3. A polycyclic aromatic compound as defined by claim 1, wherein formula (I), Ar has the structure (b).

4. A polycyclic aromatic compound as defined by claim 1, wherein formula (I), Ar has the structure (c).

5. A polycyclic aromatic compound as defined by claim 1, wherein formula (I), Ar has the structure (d).

6. A polycyclic aromatic compound as defined by claim 1, wherein formula (I), Ar has the structure (e).

7. A polycyclic aromatic compound as defined by claim 1, wherein formula (I), Ar has the structure (f).

8. A polycyclic aromatic compound as defined by claim 1, wherein formula (I), Ar has the structure (g).

9. A polycyclic aromatic compound as defined by claim 1, wherein formula (I), Ar has the structure (h).

10. A polycyclic aromatic compound as defined by claim 1, wherein formula (I), Ar has the structure (i).

11. A polycyclic aromatic compound as defined by claim 1, comprising a pharmaceutically acceptable salt thereof.

12. A polycyclic aromatic compound as defined by claim 1, wherein formula (I), Ar has the structure (a) or (i), $R_6$ is a radical —$OR_7$, and $R_2$ and $R_3$ together form, with the adjacent naphthalene nucleus from which they depend, a six-membered ring substituted by at least one methyl group.

13. A polycyclic aromatic compound as defined by claim 1, wherein formula (I), the lower alkyl radical substituents are selected from among methyl, ethyl, isopropyl, butyl, tert-butyl and hexyl radicals.

14. A polycyclic aromatic compound as defined by claim 1, wherein formula (I), the linear or branched alkyl radical substituents having from 1 to 20 carbon atoms are selected from among methyl, ethyl, propyl, 2-ethylhexyl, octyl, dodecyl, hexadecyl and octadecyl radicals.

15. The polycyclic aromatic compound as defined by claim 1, wherein formula (I), the cycloaliphatic radicals are selected from among 1-methylcyclohexyl and 1-adamantyl radicals.

16. A polycyclic aromatic compound as defined by claim 1, wherein formula (I), the monohydroxyalkyl radical substituents are selected from among 2-hydroxypropyl and 3-hydroxypropyl radicals.

17. A polycyclic aromatic compound as defined by claim 1, wherein formula (I), the polyhydroxyalkyl radical substituents are selected from among 2,3-dihydroxypropyl, 2,3,4-trihydroxybutyl, 2,3,4,5-tetrahydroxypentyl and pentaerythritol radicals.

18. A polycyclic aromatic compound as defined by claim 1, wherein formula (I), the aryl radical substituents are selected from among phenyl radicals optionally substituted by at least one halogen atom, or a hydroxyl or nitro functional group.

19. A polycyclic aromatic compound as defined by claim 1, wherein formula (I), the aralkyl radical substituents are selected from among benzyl and phenethyl radicals optionally substituted by at least one halogen atom, or a hydroxyl or nitro functional group.

20. A polycyclic aromatic compound as defined by claim 1, wherein formula (I), the alkenyl radical substituents have from 1 to 5 carbon atoms and comprise at least one site of ethylenic unsaturation.

21. A polycyclic aromatic compound as defined by claim 1, wherein formula (I), the sugar residue substituents are selected from among those of glucose, galactose, mannose and glucuronic acid.

22. A polycyclic aromatic compound as defined by claim 1, wherein formula (I), the amino acid residue substituents are selected from among those of lysine, glycine and aspartic acid.

23. A polycyclic aromatic compound as defined by claim 1, wherein formula (I), the peptide residue substituents are those of a dipeptide or tripeptide.

24. A polycyclic aromatic compound as defined by claim 1, wherein formula (I), the heterocyclic radical substituents are selected from among piperidino, morpholino, pyrrolidino and piperazino radicals which are optionally substituted by a $C_1$-$C_6$ alkyl radical or a mono- or polyhydroxyalkyl radical.

25. A polycyclic aromatic compound as defined by claim 1, wherein formula (I), the halogen atom substituents are selected from among fluorine, chlorine and bromine atoms.

26. A polycyclic aromatic compound as defined by claim 1, selected from among ethyl 2-(5,6,7,8-tetrahydro-5,5,8,8-tetramethyl-2-anthryl)-4-thiophenecarboxylate; 2-(5,6,7,8-tetrahydro-5,5,8,8-tetramethyl-2-anthryl)-4-thiophenecarboxylic acid; methyl 4-(5,6,7,8-tetrahydro-5,5,8,8-tetramethyl-2-anthryl)-2-thiophenecarboxylate; 4-(5,6,7,8-tetrahydro-5,5,8,8,-tetramethyl-2-anthryl)-2-thiophenecarboxylic acid; ethyl 6-(5,6,7,8-tetrahydro-5,5,8,8-tetramethyl-2-anthryl)nicotinate; 6-(5,6,7,8-tetrahydro-5,5,8,8-tetramethyl-2-anthryl)nicotinic acid; N-methyl-4-(5,6,7,8-tetrahydro-5,5,8,8-tetramethyl-2-anthryl)-2-pyrrolecarboxylic acid; 4-(5,6,7,8-tetrahydro-5,5,8,8-tetramethyl-2-anthryl)-2-pyrrolecarboxylic acid; methyl 2-hydroxy-4-(5,6,7,8-tetrahydro-5,5,8,8-tetramethyl-2-anthryl)benzoate; 2-hydroxy-4-(5,6,7,8-tetrahydro-5,5,8,8-tetramethyl-2-anthryl)benzoic acid; 2-methoxy-4-(5,6,7,8-tetrahydro-5,5,8,8-tetramethyl-2-anthryl)benzoic acid; 2-hydroxy-4-[7-(1-adamantyl)-6-benzyloxy-2-naphthyl]benzoic acid; 2-hydroxy-4-[7-(1-adamantyl)-6-hydroxy-2-naphthyl]benzoic acid; 2-hydroxy-4-[7-(1-adamantyl)-6-hexyloxy-2-naphthyl]benzoic acid; 4-[7-(1-adamantyl)-6-methoxyethoxymethoxy-2-naphthyl]benzoic acid; 3-methyl-4-(5,6,7,8-tetrahydro-5,5,8,8-tetramethyl-2-anthryl)benzoic acid; N-propyl-4-(5,6,7,8-tetrahydro-5,5,8,8-tetramethyl-2-anthryl)-2-pyrrolecarboxylic acid; 2-propyloxy-4-(5,6,7,8-tetrahydro-5,5,8,8-tetramethyl-2-anthryl)benzoic acid; 2-hexyloxy-4-(5,6,7,8-tetrahydro-5,5,8,8-tetramethyl-2-anthryl)benzoic acid; 5-[7-(1-adamantyl)-6-benzyloxy-2-naphthyl]-2-thiophenecarboxylic acid; 4-[7-(1-adamantyl)-6-benzyloxy-2-naphthyl]benzoic acid; 2-chloro-4-(5,6,7,8-tetrahydro-5,5,8,8-tetramethyl-2-anthryl)benzoic acid; 2-hydroxy-4-[7-(1-adamantyl)-6-(4-fluorobenzyl)oxy-2-naphthyl]benzoic acid; 2-[7-(1-adamantyl)-6-hydroxy-2-naphthyl]-4-thiophenecarboxylic acid; 2-[7-(1-adamantyl)-6-methoxy-2-naphthyl]-4-thiophenecarboxylic acid; and methyl 4-[7-(1-adamantyl)-6-benzyloxycarbonyl-2-naphthyl]benzoate.

27. A pharmaceutical composition of matter, comprising a therapeutically effective amount of a polycyclic aromatic compound as defined by claim 1, or pharmaceutically acceptable salt or isomer thereof, and a pharmaceutically acceptable carrier or diluent therefor.

28. The pharmaceutical composition as defined by claim 27, further comprising a retinoid compound, a D vitamin or derivative thereof, a corticosteroid, an anti-free radical agent, an α-hydroxy or α-keto acid or derivative thereof, an ion channel blocker, or combination thereof.

29. The pharmaceutical composition as defined by claim 27, comprising a tablet, a capsule, a syrup, a suspension, an elixir, a solution, a powder, granules, an emulsion, microspheres, nanospheres, lipid vesicles, polymeric vesicles, or an injectable.

30. The pharmaceutical composition as defined by claim 27, comprising an ointment, a cream, a milk, a pommade, an impregnated pad, a gel, a spray, or a lotion.

31. The pharmaceutical composition as defined by claim 27, adopted for topical administration.

32. The pharmaceutical composition as defined by claim 27, adopted for systemic administration.

33. The pharmaceutical composition as defined by claim 27, comprising from 0.001% to 5% by weight of said polycyclic aromatic compound, or salt or isomer thereof.

34. A method for treating a keratinization disorder in a mammalian organism in need of such treatment, comprising administering to such organism a therapeutically effective amount of the pharmaceutical composition as defined by claim 27.

35. A method for treating a dermalotogical disorder in a mammalian organism in need of such treatment, comprising administering to such organism a therapeutically effective amount of the pharmaceutical composition as defined by claim 27.

36. A method for treating an ophthalmological disorder in a mammalian organism in need of such treatment, comprising administering to such organism a therapeutically effective amount of the pharmaceutical composition as defined by claim 27.

37. A method for treating skin aging in a mammalian organism in need of such treatment, comprising administering to such organism a therapeutically effective amount of the pharmaceutical composition as defined by claim 27.

38. A method for treating epidermal and/or dermal atrophy in a mammalian organism in need of such treatment, comprising administering to such organism a therapeutically effective amount of the pharmaceutical composition as defined by claim 27.

39. A method for treating a cicatrization disorder in a mammalian organism in need of such treatment, comprising administering to such organism a therapeutically effective amount of the pharmaceutical composition as defined by claim 27.

40. A method for treating a sebaceous function disorder in a mammalian organism in need of such treatment, comprising administering to such organism a therapeutically effective amount of the pharmaceutical composition as defined by claim 27.

41. A method for treating a cancerous or precancerous disease state in a mammalian organism in need of such treatment, comprising administering to such organism a therapeutically effective amount of the pharmaceutical composition as defined by claim 27.

42. A method for treating inflammation in a mammalian organism in need of such treatment, comprising administering to such organism a therapeutically effective amount of the pharmaceutical composition as defined by claim 27.

43. A method for treating a viral infection in a mammalian organism in need of such treatment, comprising administering to such organism a therapeutically effective amount of the pharmaceutical composition as defined by claim 27.

44. A method for treating or preventing alopecia in a mammalian organism in need of such treatment, comprising administering to such organism a therapeutically effective amount of the pharmaceutical composition as defined by claim 27.

45. A method for treating a cardiovascular disorder in a mammalian organism in need of such treatment, comprising administering to such organism a therapeutically effective amount of the pharmaceutical composition as defined by claim 27.

46. A method for treating an immune deficiency in a mammalian organism in need of such treatment, comprising administering to such organism a therapeutically effective amount of the pharmaceutical composition as defined by claim 27.

47. A method for treating a dermatological, rheumatic, respiratory, cardiovascular or ophthalmologic disorder in a mammalian organism in need of such treatment, comprising administering to such organism a therapeutically effective amount of the pharmaceutical composition as defined by claim 27.

48. The method as defined by claim 47, comprising administering to such organism a daily dose of said polycyclic aromatic compound of about 0.01 mg/kg to 100 mg/kg of body weight thereof.

49. A cosmetic composition of matter, comprising a cosmetically effective amount of a polycyclic aromatic compound as defined by claim 1, or cosmetically acceptable salt or isomer thereof, and a cosmetically acceptable carrier or diluent therefor.

50. The cosmetic composition as defined by claim 49, comprising a cream, a milk, a lotion, a gel, microspheres, nanospheres, lipid vesicles, polymeric vesicles, a soap, or a shampoo.

51. The cosmetic composition as defined by claim 49, comprising from 0.001% to 3% by weight of said polycyclic aromatic compound, or salt or isomer thereof.

52. The cosmetic composition as defined by claim 49, further comprising a retinoid compound, a D vitamin or derivative thereof, a corticosteroid, an anti-free radical agent, an α-hydroxy or α-keto acid or derivative thereof, an ion channel blocker, or combination thereof.

53. A method for treating a skin or hair disorder on a mammalian organism in need of such treatment, comprising administering to such organism a cosmetically/therapeutically effective amount of the cosmetic composition as defined by claim 49.

54. The pharmaceutical composition as defined by claim 27, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

55. The pharmaceutical composition as defined by claim 27, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

56. The cosmetic composition by claim 49, further comprising a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11,-eicosatrynoic acid or ester or amide thereof, or combination thereof.

57. The cosmetic composition as defined by claim 49, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *